United States Patent
Kato et al.

(10) Patent No.: US 8,363,781 B2
(45) Date of Patent: Jan. 29, 2013

(54) NONDESTRUCTIVE IDENTIFICATION METHOD AND NONDESTRUCTIVE IDENTIFICATION DEVICE

(75) Inventors: Masayo Kato, Yokohama (JP); Koichi Nittoh, Yokohama (JP); Hitoshi Sakai, Yokohama (JP); Chikara Konagai, Yokohama (JP); Katsumi Hosaka, Chigasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 470 days.

(21) Appl. No.: 12/597,072

(22) PCT Filed: Apr. 23, 2008

(86) PCT No.: PCT/JP2008/001071
§ 371 (c)(1),
(2), (4) Date: Oct. 22, 2009

(87) PCT Pub. No.: WO2008/132845
PCT Pub. Date: Nov. 6, 2008

(65) Prior Publication Data
US 2010/0119037 A1  May 13, 2010

(30) Foreign Application Priority Data

Apr. 23, 2007 (JP) ................... 2007-113169

(51) Int. Cl.
- *G01N 23/06* (2006.01)
- *G01N 23/04* (2006.01)
- *G06K 9/00* (2006.01)

(52) U.S. Cl. .......................... 378/53; 382/141
(58) Field of Classification Search .............. 378/53, 378/57, 98, 7, 95, 62; 382/141, 128, 131, 382/132
See application file for complete search history.

(56) References Cited

U.S. PATENT DOCUMENTS
(Continued)

FOREIGN PATENT DOCUMENTS

| JP | 63-064298 A | 3/1988 |
| JP | 5-069280 B2 | 9/1993 |

(Continued)

OTHER PUBLICATIONS

Masayo Nakane, et al., "Development of nondestructive identification method for material using color x-ray imaging system", Environmental Aspects of the Management of Radioactive Waste, Transactions of the American Nuclear Society, Nov. 12-16, 2006., vol. 95, pp. 211 to 212.

(Continued)

*Primary Examiner* — Irakli Kiknadze
(74) *Attorney, Agent, or Firm* — Foley & Lardner LLP

(57) ABSTRACT

A nondestructive identification device includes: a radiation source 1 irradiating an x-ray 2 to a standard sample 5 made of a known material and a sample 3; a sensor 4 detecting a radiation ray having transmitted the standard sample 5 and the sample 3; a signal processing device 7 converting a signal of the sensor 4 into an image; an image processing device 8 which performs adjustment on an entire second image to make a luminance value of a part of the standard sample 5 in the obtained image or a relation between the luminance value and a thickness of the standard sample 5 in a first image where the energy of the radiation source 1 is first energy be the same as that in the second image where the energy of the radiation source 1 is second energy, and which performs a computation processing to take a difference or a ratio between the adjusted second image and the first image; and a display device 9 displaying an image.

11 Claims, 10 Drawing Sheets

U.S. PATENT DOCUMENTS

| | | | |
|---|---|---|---|
| 4,703,496 A | 10/1987 | Meccariello et al. | |
| 5,602,896 A | 2/1997 | Diepstraten | |
| 5,838,758 A * | 11/1998 | Krug et al. | 378/53 |
| 5,910,972 A * | 6/1999 | Ohkubo et al. | 378/54 |
| 6,263,044 B1 * | 7/2001 | Joosten | 378/98.7 |
| 6,999,609 B2 * | 2/2006 | Eck et al. | 382/132 |

FOREIGN PATENT DOCUMENTS

| | | |
|---|---|---|
| JP | 7-209493 A | 8/1995 |
| JP | 9-510068 A | 10/1997 |
| JP | 3078143 B2 | 8/2000 |
| JP | 3193665 B2 | 7/2001 |
| JP | 3595303 B2 | 2/2004 |
| JP | 3880855 B2 | 2/2007 |
| WO | WO 96/19893 A1 | 6/1996 |

OTHER PUBLICATIONS

Masayo Nakane, et al., "Development of nondestructive identification method for material of nuclear waste drums", Atomic Energy Society of Japan, Aki no Taikai Yokoshu (CD-ROM), Aug. 17, 2006, E34, p. 238.

* cited by examiner

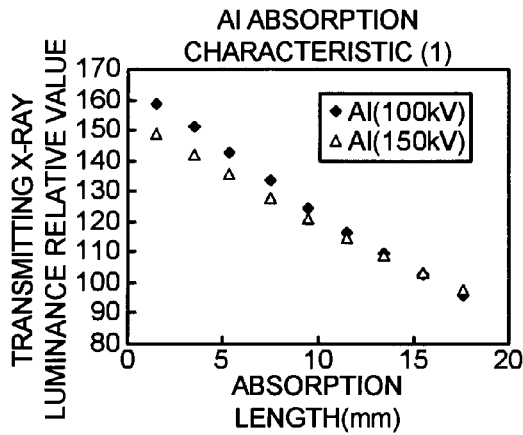
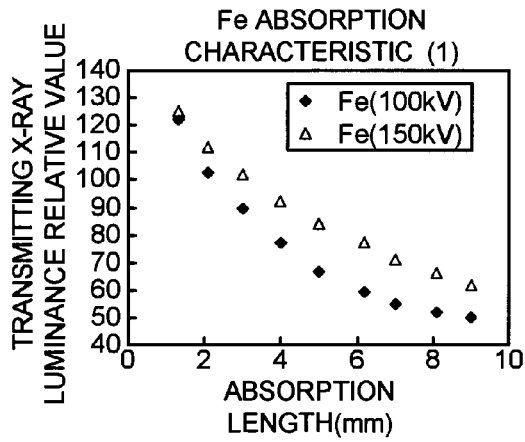
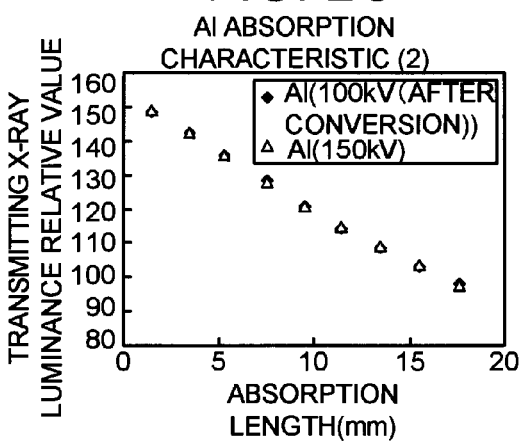
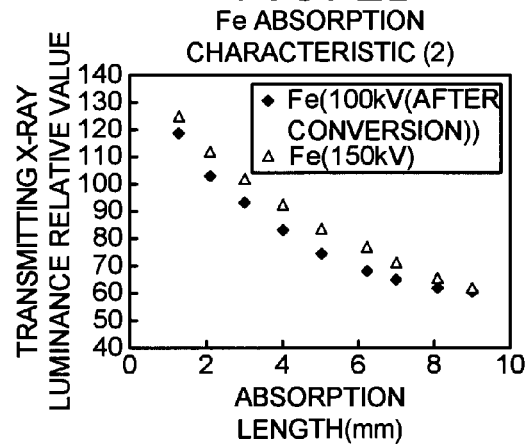
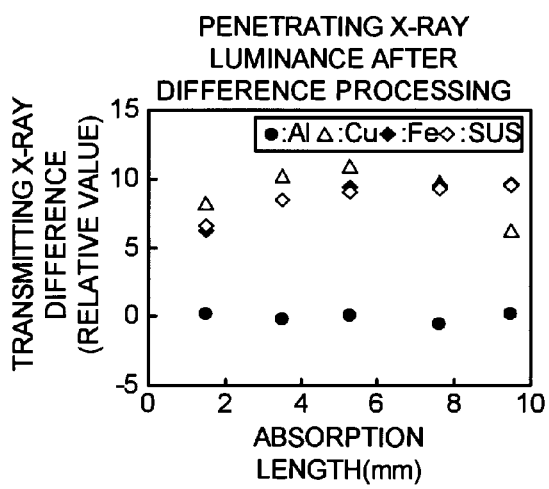

TUBE VOLTAGE 100kV

TUBE VOLTAGE 150kV

NONDESTRUCTIVE IDENTIFICATION METHOD AND NONDESTRUCTIVE IDENTIFICATION DEVICE

TECHNICAL FIELD

The present invention relates to a nondestructive identification method and nondestructive identification device for identifying an unknown substance in a container nondestructively by using an x-ray or a γ-ray.

BACKGROUND ART

When an x-ray or a γ-ray penetrates a substance, absorption and scattering differ depending on a type and a shape of a constituent substance. Recording the above as a picture such as a photo, a video, and a digital file enables obtaining a broken state, change, a packing condition or the like of the substance. This method is generally used as a method for examining a state of the inside of a human body by an x-ray picture. The above method for measuring a state of the inside without destructing a substance or a sample which is desired to be measured is called radiography or a nondestructive radiation imaging method.

In x-ray photographing used for medical diagnosis or industrial nondestructive inspection, usually an x-ray film is combinedly used with a radiation intensifying screen in order to improve sensitivity of photographing system. In x-ray photographing, silver particles on the film are directly blackened by an x-ray transmitting a sample, and besides, the x-ray is converted into a visible light in the intensifying screen and the light blackens silver particles on the x-ray film, whereby a transmission image of the sample is obtained.

There is a method in which a line sensor is used as a sensor and a subject is scanned by the line sensor when the subject passes, so that a transmission image is measured nondestructively, as in baggage inspection at an airport. In such nondestructive inspection methods using an x-ray, in a case of a composite material or in a case that thicknesses of samples to be transmitted are quite different, a transmitted radiation dosage becomes extremely large or small depending on parts, so that a larger radiation dosage flows to a smaller radiation dosage part, causing a phenomenon called fog or halation and making a result of photographing hard to view. As a method for solving such a phenomenon, there are suggested methods in which a sensitivity region of a sensor is enlarged by color information and so on.

In an atomic power plant or the like, radioactive waste is filled and stored in a sealed vessel such as a drum and a container. A stored amount thereof is increasing recently and volume reduction is required. Since a processing method for volume reduction differs depending on a material, it is necessary to sort contents by material, but there is a risk in a sorting operation. When the radioactive waste and the drum as a whole undergo a melting process, for example, a plasma melting process, an operator opens the drum and takes out the radioactive waste in the drum to sort. Since aluminum and lead in particular are not suitable for the melting process, it is necessary that aluminum and lead are stored without undergoing the melting process. It is because if aluminum undergoes the melting process and is solidified with concrete, there is a possibility that moisture in the concrete and aluminum react to generate hydrogen and damages a melting furnace. Further, if lead is molten, toxic gas is generated unpreferably in terms of pollution prevention. Therefore, when the melting process in particular is performed, a method and a device which can easily judge that aluminum or lead does not exist in the drum nondestructively are desired.

As an example of a conventional sorting process of waste as described above, there is a method in which whether or not a metal exists in the waste is sorted by a metal detector and further whether a shape of the metal is indefinite or definite is sorted by an x-ray inspection device (for example, see Reference 1). In addition, there is a method in which a component of radioactive waste moving on a roller conveyer is found out by combination of a capture γ-ray analyzing device and a fluorescent x-ray analyzing device (for example, see Reference 2). The former technique of the above conventional techniques cannot identify types of the metals, while the latter technique can identify a material but opening is required. On the other hand, as a method for judging materials of contents nondestructively, there is an x-ray CT method. In the x-ray CT method, an x-ray absorption rate, that is, an x-ray absorption coefficient of each waste is obtained and a thickness of each waste is obtained, whereby the material of each waste can be judged. However, in this method, a device constitution becomes complicated for the sake of data collection, image reconstruction computation, displaying, or the like, thus leading to a high cost.

As a method for solving the above, there is a following method. In this method, by using an n x-ray tube voltage as a parameter, an x-ray transmission image tone value or a function thereof is detected to be a reference tone for every material. The reference tone can be also obtained by calculation and is registered as a data table. A sample is measured and compared with the reference tone registered as a database in advance, whereby a material is specified. In this method, identification of lead and aluminum in particular can be performed more easily than in an x-ray CT (for example, see Reference 3). However, in this method, there are problems that when different materials overlap with each other in a perspective direction, it is difficult to judge from a reference function for every material, and when a thickness is different from that in the reference function, judgment is also difficult, and so on. Further, in this method, by using thickness dependence of x-ray transmission by material by an x-ray tube voltage (same as energy, but strictly, not equal because it has a distribution) as a parameter, judgment is done based on an obtained luminance value. However, in a case that the tube voltage is used as the parameter, discriminable luminance data cannot be obtained unless a tube current is simultaneously used as a parameter. For example, in a case of a tube current of data of 300 kV and a tube current of data of 100 kV, similar luminance cannot be obtained unless the tube current of 100 kV is increased. Therefore, it is necessary to have large data for every material as a table, and in order to perform accurate judgment, a measurement condition of a sample must be the same as a condition under which a database is obtained. However, in a case of waste, materials and sizes of contents vary, and photographing cannot be always done under the same condition. Therefore, there is a problem that the database is required to be remeasured every time the measuring condition is altered.

Reference 1: JP-A 6-273588 (KOKAI)
Reference 2: JP-A 7-209493 (KOKAI)
Reference 3: Japanese Patent JP-B2 3193665

DISCLOSURE OF THE INVENTION

In a method of performing nondestructive identification inspection of a composite material conventionally as described above, it is necessary to measure information with different thicknesses by material and transmission luminance data by a tube voltage of an x-ray in advance, and to compare luminance data of a sample to be identified and change in an image luminance value at a time that a tube voltage is changed with change of data made to be a database in advance, so that a material is identified. Besides, when materials overlap with each other (for example, iron and aluminum, and the like) as in a case of a composite material, it is difficult to identify the material from luminance change even by the above method. Further, data of a tube voltage as well as a material and a thickness of the material which is registered in advance has, unsimilarly to single-colored energy as a γ-ray, an energy distribution with wide broadening in a situation that an x-ray is unstable, and thus there is a problem that it is practically difficult to obtain stable and reproducible luminance data.

The present invention is made in view of the above-described problems in the conventional techniques, and an object thereof is to provide a nondestructive identification method and a nondestructive identification device by which identification of a material of a sample can be done more easily than conventionally done without destroying an object to be inspected.

(Means for Solving the Problems)

A nondestructive identification method according to the present invention in which a radiation ray of an x-ray or a γ-ray is irradiated from a radiation source to a sample and contents inside the sample are identified from a transmission image of the radiation ray having transmitted the sample includes: obtaining a first transmission image by irradiating the radiation ray to the sample and one or more standard samples made of a known material, with energy of the radiation source being first energy; obtaining a second transmission image by irradiating a radiation ray to the sample and the one or more standard samples, with the energy of the radiation source being second energy different from the first energy; performing luminance adjustment on the second transmission image to make a luminance value of a part of the standard sample in the second transmission image be almost the same as a luminance value of a part of the standard sample in the first transmission image; and obtaining an image in which only a part of the same material as the standard sample is deleted, by taking a difference between the second transmission image on which the luminance adjustment is performed and the first transmission image.

Further, another nondestructive identification method according to the present invention in which a radiation ray of an x-ray or a γ-ray is irradiated from a radiation source to a sample and contents inside the sample are identified from a transmission image of the radiation ray having transmitted the sample includes: by photographing a transmission image of a standard sample of known thickness and material and the sample while sequentially adding the standard samples with energy of the radiation source being first energy, and by photographing a transmission image of the standard sample and the sample while sequentially adding the standard samples with energy of the radiation source being second energy different from the first energy, obtaining a relation between the thickness of the standard sample in two types of energy and a luminance value of the transmitting radiation ray, and obtaining a function to make the luminance value obtained with the first energy in the transmission image of the standard sample be almost the same as the luminance value obtained with the second energy; and by taking a ratio between an image made by applying the function to the entire transmission image obtained with the first energy and a transmission image obtained with the second energy, normalizing a luminance of a part of the standard sample to be a specific value.

Further, still another nondestructive identification method according to the present invention in which a radiation ray of an x-ray or a γ-ray is irradiated from a radiation source to a sample and contents inside the sample are identified from a transmission image of the radiation ray having transmitted the sample includes: by photographing a transmission image of a standard sample of known thickness and material and a sample while sequentially adding the standard samples, with energy of the radiation source being first energy, and by photographing a transmission image of the standard sample and the sample while sequentially adding the standard samples with energy of the radiation source being second energy different from the first energy, obtaining a relation between the thickness of the standard sample and a luminance value of the transmitting radiation ray in two types of energy; and by comparing the relation of the luminance value for the thickness of the standard samples added before the sample and the relation between the thickness and the luminance value in only the standard sample, speculating a material and a thickness of the sample.

A nondestructive identification device according to the present invention includes: one or more standard samples made of a known material; a radiation source irradiating a radiation ray of an x-ray or a γ-ray to the standard sample and a sample and whose energy can be changed; a sensor detecting the radiation ray having transmitted the standard sample and the sample; a signal processing device converting a signal of the sensor into an image; an image processing device which performs adjustment on an entire second image to make a luminance value of a part of the standard sample in the image obtained by the signal processing device or a relation between the luminance value and a thickness of the standard sample in a first image where the energy of the radiation source is first energy be the same as that in the second image where the energy of the radiation source is second energy different from the first energy, and which performs a computation processing to take a difference or a ratio between the adjusted second image and the first image; and a display device displaying an image on which the computation processing is performed by the image processing device.

Further, another nondestructive identification device according to the invention includes: a standard sample of known material and thickness; a radiation source irradiating a radiation ray of an x-ray or a γ-ray to the standard sample and a sample and whose energy can be changed; a sensor detecting the radiation ray having transmitted the standard sample and the sample; a signal processing device converting a signal of the sensor into an image; wherein the thickness of the standard sample and the energy of the radiation source are changed and a transmission image is measured each time, and a material and a thickness of the sample is derived from change of a luminance of the image by the thickness of the standard sample and the energy of the radiation source.

BRIEF DESCRIPTION OF THE DRAWINGS

FIG. 2A to FIG. 2E are characteristic charts for explaining a relation between an absorption length and a transmitting x-ray luminance in Al and Fe.

BEST MODE FOR IMPLEMENTING THE INVENTION

Hereinafter, details of the invention will be described in embodiments with reference to the drawings. First, a first embodiment will be described with reference to FIG. 1.

Figure 1:
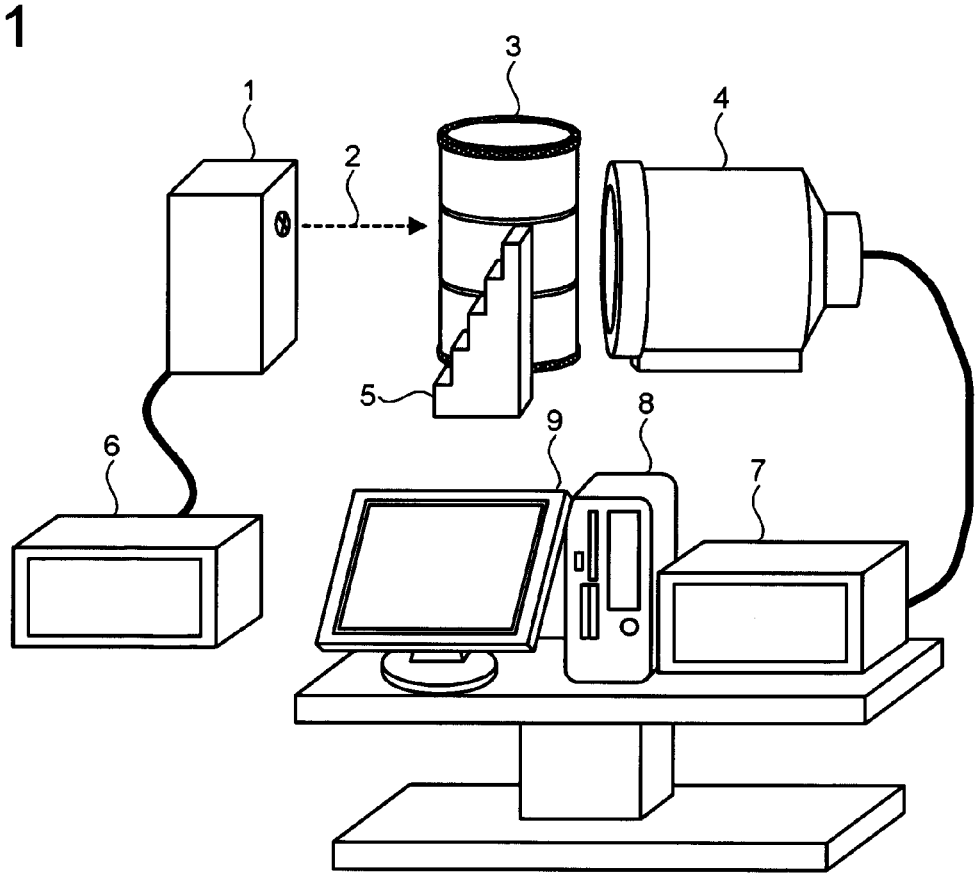
FIG. 1 is a schematic diagram showing a constitution of a nondestructive identification device according to an embodiment of the present invention.

FIG. 1 shows a constitution of a nondestructive identification device according to the first embodiment. As shown in FIG. 1, the nondestructive identification device of the present embodiment includes a standard sample 5 made of a known material, a radiation source 1 irradiating an x-ray 2 to the standard sample 5 and a sample 3, a sensor 4 detecting a radiation ray having transmitted the standard sample 5 and the sample 3, a signal processing device 7 converting a signal of the sensor 4 into an image, an image processing device (personal computer) 8 which performs adjustment on an entire second image so that a luminance value of a standard sample 5 part in the image obtained by the signal processing device 7 or a relation between the luminance value and a thickness of the standard sample 5 in a first image where energy of the radiation source 1 is first energy is the same as that in the second image where energy of the radiation source 1 is second energy different from the first energy, and which performs a computation processing to take a difference or a ratio between the adjusted second image and the first image, and a display device 9 displaying an image. Further, the radiation source 1 can adjust a tube voltage and a tube current by an x-ray generator controller 6.

The x-ray 2 irradiated from the x-ray radiation source 1 penetrates the sample 3 and the standard sample 5 made of the known material, and is measured by the sensor 4. It should be noted that though the x-ray is used in the present embodiment, a γ-ray can be also used. The sensor 4, being an area sensor such as an x-ray image intensifier, receives the x-ray having transmitted the sample 3 and the standard sample 5, and transmits an output signal thereof to the signal processing device 7. The output signal is converted into an image by the signal processing device 7 and transmitted to the image processing device 8. The image processing device 8 performs an image processing on the obtained image and identifies a material.

Transmission of an x-ray through a substance can be represented as below with an intensity before incident to the substance being $I_0$ and an intensity after transmission being I.

$$I = I_0 \exp(-\mu \rho t) \quad (1)$$

Here, $\mu$ (cm$^2$/g) indicates a mass energy absorption coefficient depending on energy of an x-ray, $\rho$ (g/cm$^3$) indicates a density of a transmitted substance, and t (cm) indicates a thickness which the x-ray (γ-ray) penetrates. In a case of a γ-ray, since energy is often represented by a single color, a mass energy absorption coefficient $\mu$ is given as a total attenuation coefficient by calculation, while in a case of an x-ray, an energy characteristic of an x-ray tube which is used is not simple colored but has a quite broad and extended spectrum (extended from a low energy to a high energy) with bad energy resolution, so that a mass energy absorption coefficient $\mu$ is not given easily by calculation and is obtained as effective energy by an experiment or the like. When assuming a case that substances with the same thickness t are measured, a transmission intensity depends on a density and a mass energy absorption coefficient of the substance.

The mass energy absorption coefficient $\mu$ varies depending on energy of an irradiated x-ray. For example, in a case of Al, a mass energy absorption coefficient for x-ray energy of 100 keV is $\mu_{Al}=0.171$ (cm$^2$/g), while a mass energy absorption coefficient for x-ray energy of 200 keV becomes smaller, that is, $\mu_{Al}=0.122$ (cm$^2$/g), and according to a formula (1), the x-ray with higher energy is easy to penetrate. A relation between the x-ray energy and the mass energy absorption coefficient differs by material.

Hereinafter, a principle of a material identification method in the present embodiment will be described by using FIG. 2A to FIG. 2E. FIG. 2A and FIG. 2B show results of measurement of x-ray absorption characteristics of Al and Fe as examples in cases of photographing with x-ray tube voltages of 100 kV and 150 kV. The fact that the tube voltages of x-rays differ means that energy of the irradiated x-rays effectively differ. Therefore, as described above, since the mass energy absorption coefficient varies when the tube voltage differs, an x-ray absorption characteristic for a thickness of a material differs.

Here, it is assumed that there is experimentally obtained a function to adjust a luminance so that data of the tube voltage of 100 kV becomes the same as data of the tube voltage of 150 kV in FIG. 2A. When the obtained function is applied to the data of the tube voltage of 100 kV, in a case of Al, the same incline is obtained as in FIG. 2C, as a matter of course. On the other hand, FIG. 2D shows a result that the above-described function is applied in a case of Fe. As shown in FIG. 2D, since Fe is different from Al in terms of a variation amount of the mass energy absorption coefficient for energy, the result is not the same as data of a tube voltage of 150 kV even if the same function is applied to data of a tube voltage of 100 kV of Fe. Therefore, when a difference between the both is taken, as shown in FIG. 2E, the difference is zero with any absorption length in the case of Al, while the difference is not zero in the case of other materials. When this processing is applied to an image, an image in which only an Al part is deleted regardless of a thickness can be obtained. It should be noted that evaluation results of SUS and Cu in addition to Fe are shown in FIG. 2E. As shown in FIG. 2E, since Fe and SUS are almost the same in terms of components, Fe and SUS show the same tendency, while Cu shows a tendency different from that of Fe.

Figure 3A:
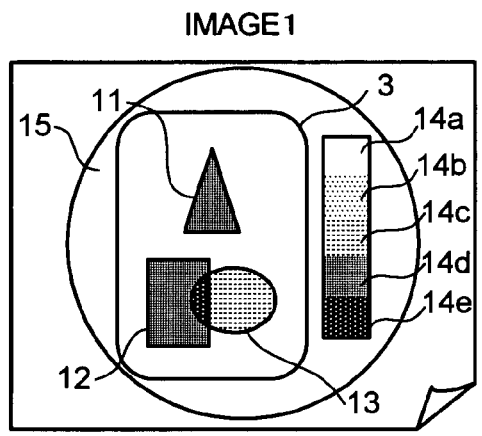
FIG. 3A to FIG. 3D are explanatory diagrams showing states of images in a nondestructive identification method.

Procedures to apply the above principle to an image processing and to apply to material identification will be described by using FIG. 3A to FIG. 3D. An image 1 in FIG. 3A is an image of a container in which contents 11, 12, 13 made of different materials and a standard sample 14 made of a known material exist, the image photographed by an image sensor such as, for example, an x-ray image intensifier. A reference numeral 15 indicates a measurable region of the image sensor. Here, it is assumed that the material of only the content 13 among the contents is different from the materials of the other contents 11, 12 but that luminances thereof coincide with one another by chance.

Figure 3B:
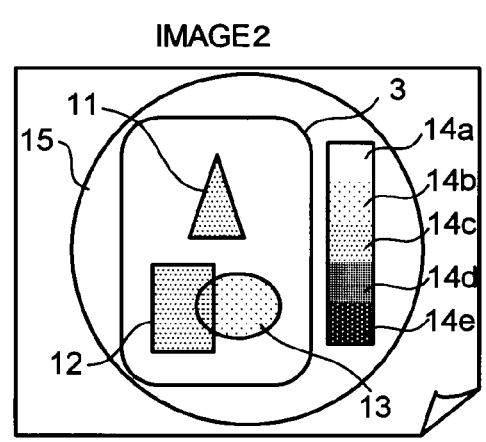

Next, an image photographed with the energy being changed is indicated as an image 2 in FIG. 3B. Since the materials of the content 11 and the content 12 are the same, variation amounts of luminances coincide with each other, while a luminance of the content 13 which has a different variation amount of an absorption coefficient is different. However, only with the above information, though it can be normally speculated that the materials of the content 11 and the content 12 are the same and that the material of the content 13 is different, it cannot be judged what the materials are. Thus, it is considered to delete the same material as that of the standard sample 14 by using an image part of the standard sample 14 which is made of the known material, the standard sample 14 having been photographed in the same screen, by the procedures explained by using FIG. 2A to FIG. 2E.

Figure 3C:
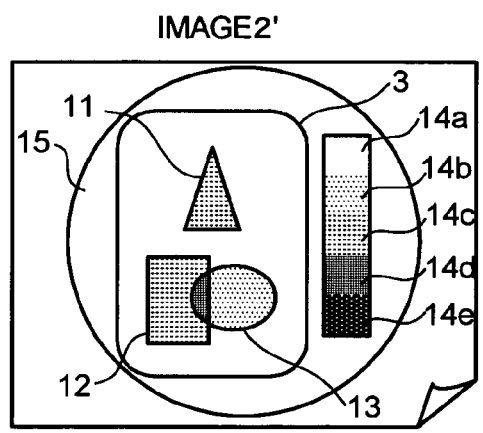
Figure 3D:
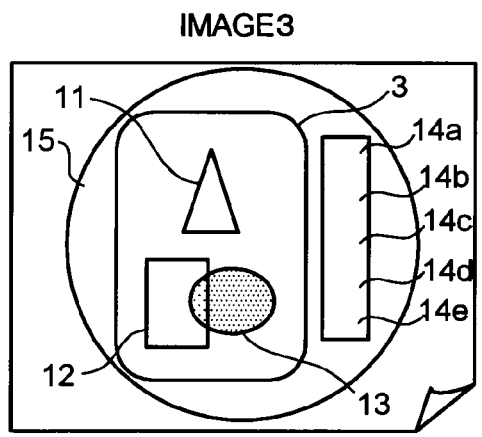

First, a function to make luminances of parts 14a to 14e in the image 1 and luminances of parts 14a to 14e in the image 2 coincide with each other is applied to the image 2, to create an image 2' in FIG. 3C. On this occasion, for example, if the materials of the content 11 and the content 12 are the same as the material of the standard sample 14, variation amounts of brightness are also the same. Thus, by applying the function, luminances of the content 11 and the content 12 in FIG. 2' coincide with the luminances of the content 11 and the content 12 in the image 1. Therefore, by taking a difference between the image 2' after conversion and the image 1, an image 3 in FIG. 3D in which the same material as the material of the standard sample 14 is deleted can be obtained. Since the material of the content 13 is different, a luminance thereof does not coincide even if the similar conversion is performed, and the content 13 is not deleted from the image 3 being a difference image. When such a processing is performed, the image 3 in which only an object with the same material as that of the standard sample 14 has been deleted can be obtained. By this method, even in a case that the content 12 and the content 13 overlap with each other, an impression of an overlapped part remains on the image, so that judgment that two materials have overlapped with each other is possible.

According to the present embodiment, it becomes possible to identify a material without photographing multiple images from different directions and without preparing a large database for every material. Further, the present embodiment can be applied to a case that a plurality of materials overlaps with each other, to such a case, a conventional technology having been difficult to be applied. By performing photographing and the image processing of the samples 11, 12, 13 and the sample 14 simultaneously, an influence of a varying background in every shooting can be eliminated, so that highly accurate measurement can be performed.

Figure 4:
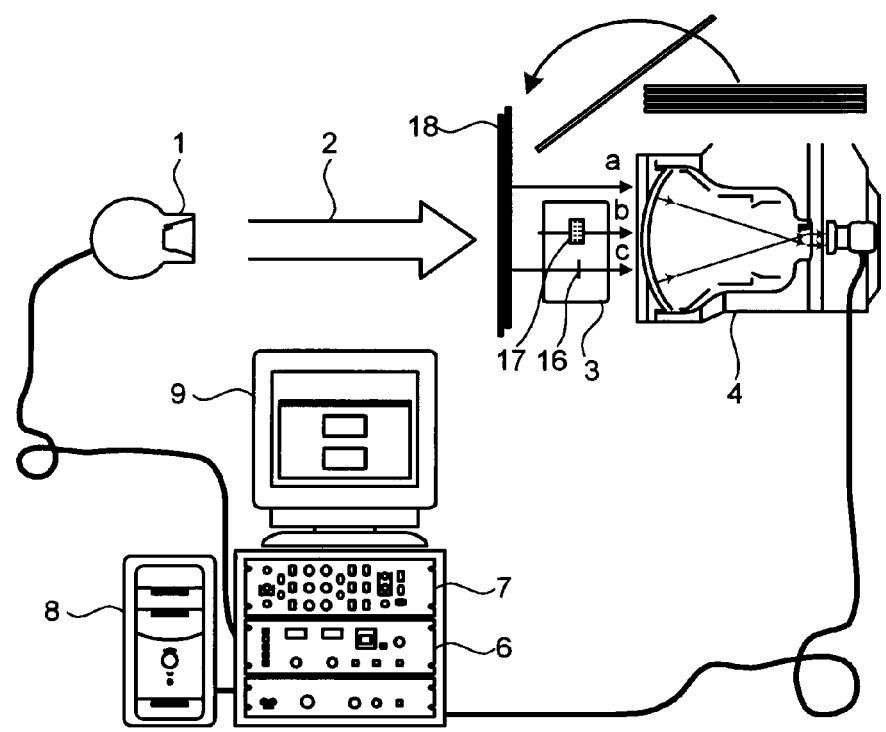
FIG. 4 is a schematic diagram showing a constitution of a nondestructive identification device according to a second embodiment of the present invention.

Next, a second embodiment will be described with reference to FIG. 4. FIG. 4 is a diagram showing a constitution of a nondestructive identification device according to the present embodiment. In FIG. 4, a reference numeral 1 indicates a radiation source generating an x-ray. An x-ray 2 emitted from the radiation source 1 is irradiated to a sample 3, and an intensity of the transmitting x-ray 2 is detected by an image intensifier 4 being a sensor. A detected signal of the image intensifier 4 is processed by a signal processing device 7 and an image processing device 8, and displayed in a monitor 9. A tube voltage and a tube current of the radiation source 1 are adjusted by an x-ray generator controller 6.

Hereinafter, a principle of a material identification method in the present embodiment will be described by using FIG. 4. In the sample 3, there are contained materials of a metal 16 whose x-ray energy absorption coefficient is large and of a metal 17 whose x-ray energy absorption coefficient is small. In order to obtain thicknesses thereof, first, with energy of the x-ray being first energy (for example, the tube voltage of the radiation source 1 being 100 kV), a transmission amount is obtained. Even if two contents are different metals, the intensities can be seen almost the same due to difference in thicknesses.

Next, when the energy of the x-ray is changed to a second energy (for example, the tube voltage of the radiation source 1 is changed to 200 kV), an entire screen becomes bright, and thus, the tube current is adjusted so that brightness in an x-ray a, which has no substance to penetrate, becomes the same as that at a time of the tube voltage of 100 kV. On this occasion, since a linear absorption coefficient varies when energy of the x-ray is different, the intensities with an x-ray b and with an x-ray c are not necessarily the same as those with 100 kV. Subsequently, metal plates 18 being standard samples are inserted so that an intensity value becomes almost the same as that at a time of 100 kV. Though a feature of the metal plate 18 is required to be clear, it is not necessary to limit the feature to iron, copper and so on. Here, a case of copper is considered. It is assumed that a thickness of the metal plates 18 is increased and that an intensity the same as that at the time of 100 kV is attained at a certain thickness. At this time, the x-ray 2 penetrates the metal plate 18, and penetrates the metal 16 or the metal 17. The transmitting x-ray 2 is divided into the x-ray a, the x-ray b, and the x-ray c, respectively, and made to an image in the image intensifier 4.

Here, a case is considered that the evaluation objects 16 and 17 are, for example, aluminum and copper. The above-mentioned $\mu$, $\rho$, $t$ in the formula (1) of the x-ray absorption characteristic are indicated as $\mu_{Al}$, $\rho_{Al}$, $t_{Al}$ for aluminum and as $\mu_{Cu}$, $\rho_{Cu}$, $t_{Cu}$ for copper, respectively.

In a case that the transmission intensities of the samples measured under a certain x-ray radiation condition are equal, the materials of the samples cannot be determined to be aluminum or copper. Under that condition, since right sides of the above-described formulas (1) are equal, the following formula (2) is possible.

$$\mu_{Al} \times \rho_{Al} \times t_{Al} = \mu_{Cu} \times \rho_{Cu} \times t_{Cu} \qquad (2)$$

$$\rho_{Al}=2.7(g/cm^3), \rho_{Cu}=8.9(g/cm^3)$$

If the x-ray radiation condition is 100 keV as effective energy, $\mu$ is given from a literature, and the followings are obtained.

$$\mu_{Al}=0.171(cm^2/g)$$

$$\mu_{Cu}=0.461(cm^2/g)$$

When these values are substituted, $$\mu_{Al} \times \rho_{Al} \times t_{Al}=0.171 \times 2.7 \times t_{Al}=0.46 \cdot t_{Al}$$

$$\mu_{Cu} \times \rho_{Cu} \times t_{Cu}=0.461 \times 8.9 \times t_{Cu}=4.1 \cdot t_{Cu}$$

are obtained and from the formula (2), the following relation is derived.

$$t_{Cu}=0.113 \cdot t_{Al} \qquad (3)$$

Therefore, in a case that the effective energy of the x-ray is 100 keV, the transmission intensity values of aluminum and copper can be regarded to be equal in a state that thicknesses are in the relation represented by the formula (3).

Next, if the x-ray radiation condition is 200 keV as effective energy, the followings are obtained.

$$\mu_{Al}=0.122(cm^2/g)$$

$$\mu_{Cu}=0.157(cm^2/g)$$

When these values are substituted, $$\mu_{Al} \times \rho_{Al} \times t_{Al} = 0.122 \times 2.7 \times t_{Al} = 0.33 \cdot t_{Al}$$

$$\mu_{Cu} \times \rho_{Cu} \times t_{Cu} = 0.157 * 8.9 * t_{Cu} = 1.4 \cdot t_{Cu}$$

are obtained and from the formula (2), the following relation is derived.

$$t_{Cu} = 0.236 \cdot t_{Al} \qquad (4)$$

Therefore, even though the luminances are equal by satisfying the formula (3) in the case of 100 keV, luminances are not equal in a case of 200 keV.

Here, there is considered an example in which the metal 16 shown in FIG. 4 with a large x-ray energy absorption coefficient is copper and the metal 17 with a small x-ray energy absorption coefficient is aluminum. In the case of the x-ray energy of 100 keV, if the relation $t_{Cu} = 0.113 \cdot t_{Al}$ is satisfied between the thickness $t_{Cu}$ of copper and the thickness $t_{Al}$ of aluminum by the above formulas (2), (3), transmission intensities are equal, so that copper and aluminum have the same brightness in the image. In such a state, aluminum and copper cannot be distinguished by the images. Thus, measurement is performed while changing energy of the x-ray to penetrate. When the energy is increased from 100 keV to 200 keV, an x-ray luminance value having transmitted copper changes from $-4.1 \cdot t_{Cu}$ to $-1.4 \cdot t_{Cu}$ exponentially and the transmission intensity is increased, so that the image becomes brighter. In order to make those images have the same brightness (transmission intensity), $$\text{by } -4.1 \cdot t_{Cu} = -1.4 \cdot (x + t_{Cu}),$$

$$x = (2.7/1.4) t_{Cu},$$

and the thickness is to be increased by $(2.7/1.4) \, t_{Cu}$.

Next, judging procedures of a material and a thickness by using the above principle will be described below. A relation between a thickness and a transmission intensity in a case of 200 keV can be obtained by sequentially adding metal plates (copper plates) 18 and measuring the luminance of the x-ray a. Next, it is assumed that when the copper plate is added by Δt cm, a luminance of the x-ray c becomes the same as the luminance of the x-ray c in the case of 100 keV. Further, it is assumed that the luminance of the x-ray a in a case of a thickness T as a result of further addition of copper plates becomes the same as the luminance of the x-ray c in the case of 100 keV.

On this occasion, if the content 16 is copper, $t_{Cu} + \Delta t = T$, so that $t_{Cu}$ is obtained. If the luminance in the case of 200 keV in the obtained $t_c$, deviates from the above-obtained relation between the thickness and the luminance, it can be judged that the content 16 is not copper. By sequentially performing a series of operations described above by using another standard substance, estimation of a material and judgment of a thickness can be done.

Figure 5A:
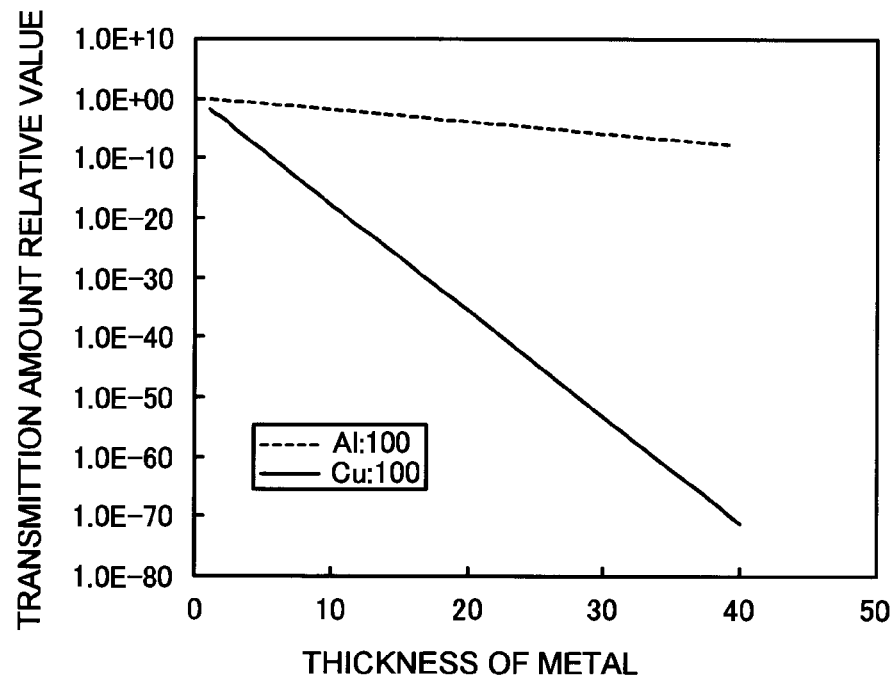
FIG. 5A and FIG. 5B are characteristic charts in which relations between absorption lengths and transmitting x-ray luminance in Al and Cu are normalized and compared.
Figure 5B:
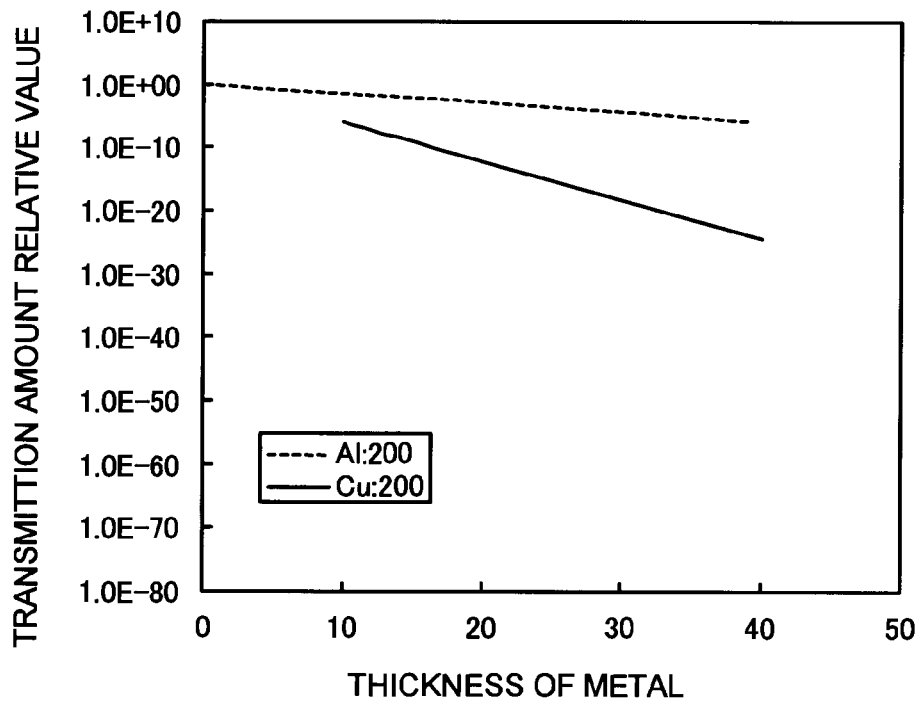
Figure 6:
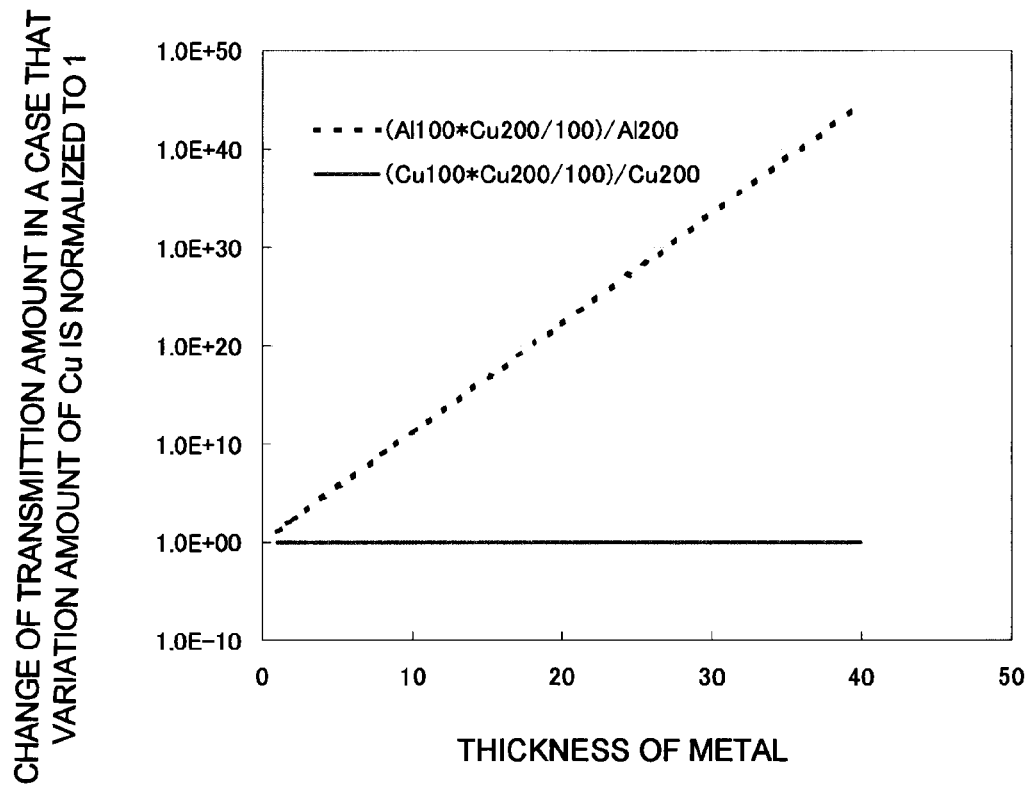
FIG. 6 is a characteristic chart showing variation of a transmission amount in a case that a variation amount of Cu is normalized to 1 (one).

If the material becomes clear by the above method, the material is not composite. Thus, a correlation between the intensity of the x-ray a and the thickness of the increased metal plates 18 at the time that the metal plates 18 are increased is to be obtained from a measurement result with different energy. For example, there is shown in FIG. 5A a graph in which a transmission luminance for thicknesses of Cu and Al is normalized in relation to a luminance for a thickness of zero in a case of energy of 100 keV, and there is shown in FIG. 5B a graph in a case of energy of 200 key. Here, a function is obtained such that an incline of Cu in the case of energy of 100 keV is similar to an incline of Cu in the case of 200 keV. This function is multiplied to entire data of energy of 100 keV and then division by data of 200 keV is performed, whereby, as shown in FIG. 6, transmission luminance data of Cu is normalized to be 1 (one) regardless of the thickness. On this occasion, in Al, since a variation amount for the thickness by energy is different as compared with that in Cu, the variation amount is large and can be obtained as luminance data.

In this method, even if copper and aluminum overlap with each other and are in a composite state, only a copper part is normalized to 1 (one) and displayed as the same luminance value, so that an overlapping part of aluminum is displayed as a different luminance value, enabling judgment as a composite material also from an image. Further, it becomes also possible to select only a part where the luminance is normalized to 1 (one) from computation of such digital image data and to display such a part by using a different color. This processing can be used also for another metal desired to be identified in similar procedures, also for iron or brass other than copper.

According to the present embodiment, only by additionally measuring a substance with a known thickness, estimation of a substance of a sample and a thickness thereof can be derived.

Figure 7A:
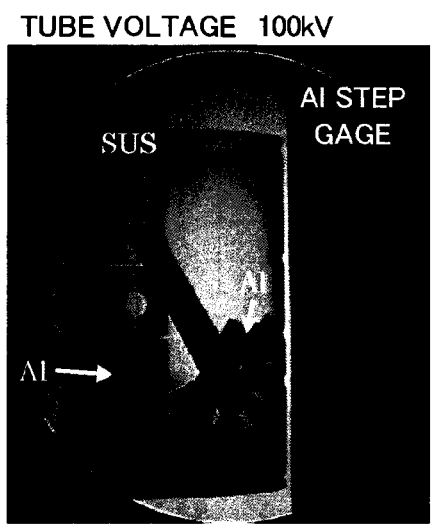
FIG. 7A to FIG. 7C are explanatory diagrams showing images having undergone a processing to delete Al from images.
Figure 7B:
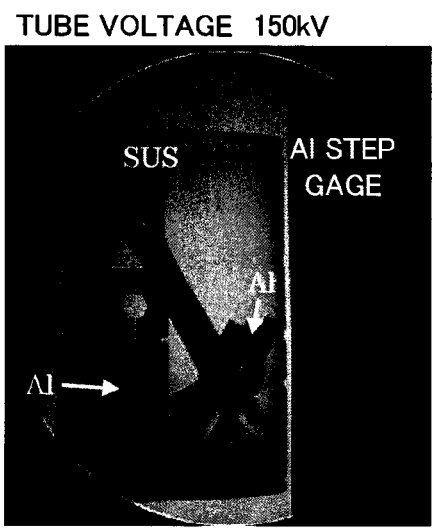
Figure 7C:
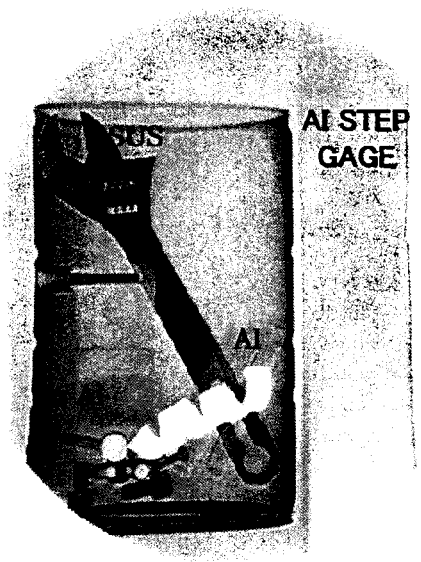

Next, a third embodiment will be described with reference to FIG. 7A to FIG. 7C. FIG. 7A to FIG. 7C show images of a sample, that is, a steel can which includes contents made of Al and SUS, with an Al step gauge being photographed simultaneously as a standard sample. FIG. 7A is the image photographed with a tube voltage being 100 kV, while FIG. 7B is the image photographed with a tube voltage being 150 kV. As a sensor, a color x-ray image intensifier is used. The color x-ray image intensifier is constituted by combining a scintillator converting a radiation into a light, an amplification function converting the emitted light into an electric signal and electrically amplifying that electric signal, a color scintillator emitting lights of a plurality of colors in correspondence with an intensity of the electric signal, and a color camera. The display images of FIG. 7A to FIG. 7C are obtained by extracting only red components among three components of red, green, and blue. Since a thickness of the content is not known, a material cannot be identified only by the images of FIG. 7A and FIG. 7B.

Thus, processings described in the first embodiment are performed to identify the material. A function by which luminance values of the Al step gauge coincide in both images of FIG. 7A and FIG. 7B is obtained, and here the function is applied to the entire image of FIG. 7A. Subsequently, the image of FIG. 7B is difference-processed from the image of FIG. 7A which has been converted so that the luminance value of the Al step gauge coincides, whereby the image in FIG. 7C is obtained. In FIG. 7C, only the Al component is deleted. In this way, for example, by deletion of only an Al material from a red component and synthesis with a green component in which Al is not deleted, an image in which only Al is displayed in green can be obtained.

By simultaneously photographing a plurality of standard samples and performing a processing to delete different materials for every component by similar procedures, it becomes possible to display materials with different colors for every material.

According to the present embodiment, it is possible to simultaneously identify materials of samples with different thicknesses instantaneously without photographing multiple images from different directions, and visibility is improved by displaying with different colors.

Figure 8:
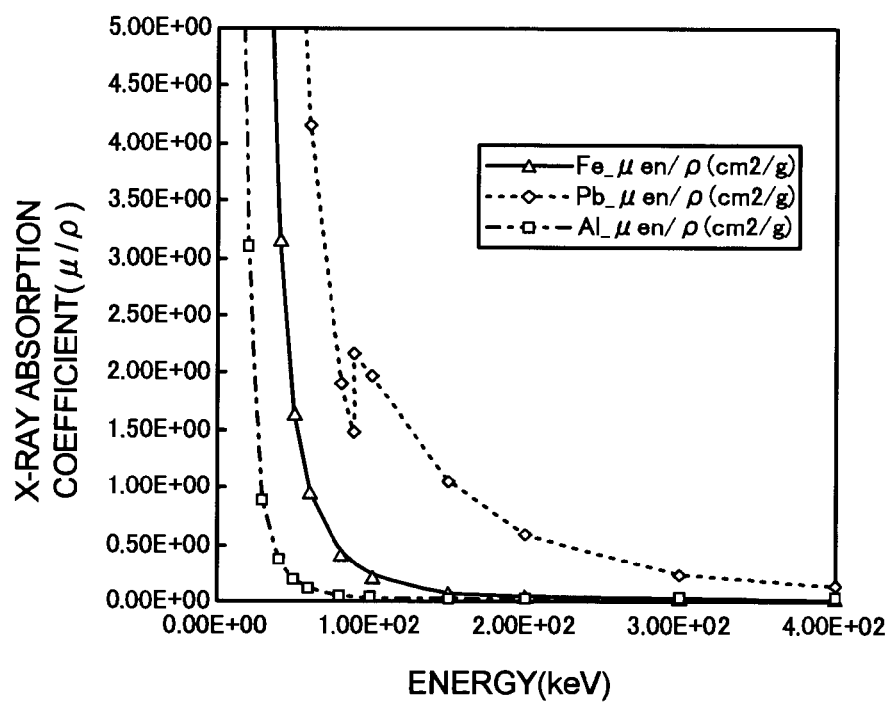
FIG. 8 is a characteristic chart showing energy dependence of x-ray absorption coefficient of Al, Fe, and Pb.

Next, a fourth embodiment will be described with reference to FIG. 8. FIG. 8 is a graph in which x-ray absorption coefficients are compared by using those of Al, Fe, and Pb as examples. In terms of a region with energy higher than a K-absorption edge of Pb, from FIG. 8, it is found that a ratio of variation of a mass absorption coefficient in relation to x-ray energy is larger as an atomic number is larger, as Pb>Fe>Al.

Figure 9A:
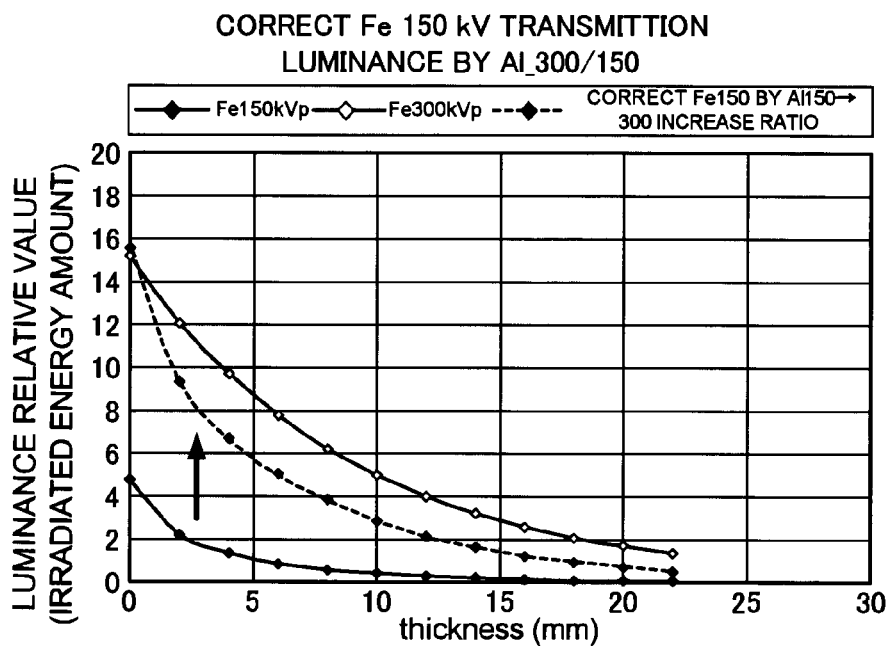
FIG. 9A and FIG. 9B are characteristic charts showing differences in variation by elements in a case that transmitting x-ray luminance adjustment is applied.

Based on the above, a speculation method of an element will be described by using FIG. 9A and FIG. 9B by using cases of Al and Fe as examples. First, two types of step gauges of Al and Fe are photographed under two types of tube voltage conditions of 300 kV and 150 kV, to obtain absorption coefficients thereof. Subsequently, a function to delete Al is obtained by using procedures explained in the first embodiment and then applied, whereby an absorption characteristic of Fe is obtained as in FIG. 9A. On the other hand, a function to delete Fe is obtained and then applied, whereby an absorption characteristic of Al is obtained as in FIG. 9B.

Since the ratio of variation of the absorption coefficient in relation to x-ray energy is Fe>Al as described above, differences in luminance in cases of 300 kV and 150 kV are larger in Fe than in Al. Thus, as shown in FIG. 9(a), even if a function to convert data of Al of 150 kV into data of 300 kV is applied to data of Fe of 150 kV, a luminance of Fe of 300 kV cannot be obtained. Therefore, (Fe 300 kVp raw data)−(Fe 150 kVp converted data)>0.

Figure 9B:
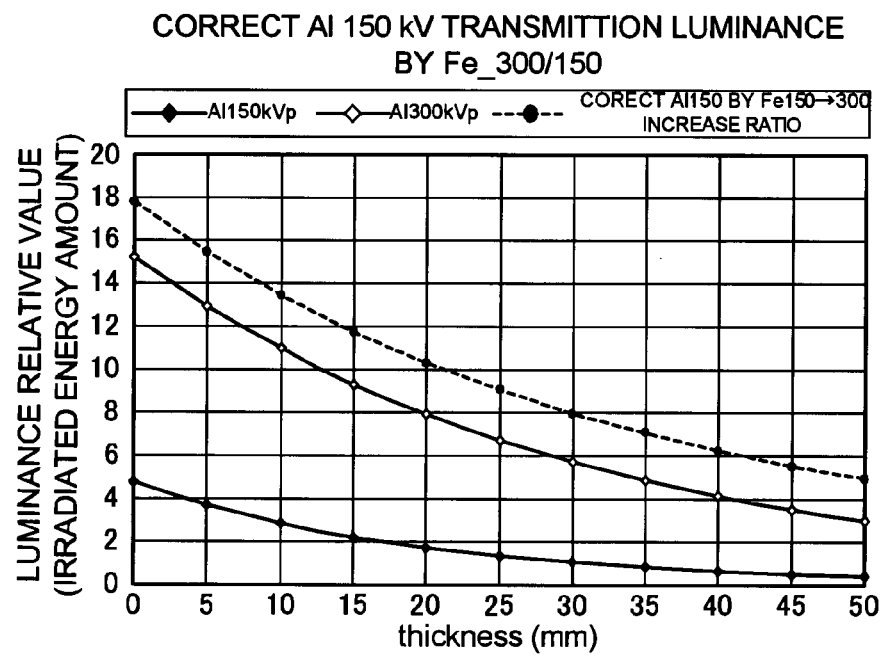

In contrast, if a function to convert data of Fe of 150 kV into data of 300 kV is applied to data of Al of 150 kV, as shown in FIG. 9B, a luminance exceeds a luminance of Al of 300 kV. Therefore, (Al 300 kVp raw data)−(Al 150 kVp converted data)<0.

By using the above, it is possible to speculate whether a constitutional element is heavier or lighter than a standard substance by whether a luminance value of a part to be measured at a time that a difference of the converted data is taken is positive or negative. Further, division can be done on the converted image, and in such a case, judgment is performed by whether the luminance of the part to be measured is larger or smaller than 1 (one). It should be noted that an x-ray absorption coefficient is a product of a density and a mass absorption coefficient, but in some materials, a magnitude relation between atomic numbers of components and a magnitude relation of densities do not necessarily coincide with each other. The judgment as above can be performed only in a case that a magnitude relation between linear absorption coefficients being products of a density and a mass absorption coefficient is the same as a magnitude relation between the mass absorption coefficients.

According to the present embodiment, by preparing and evaluating a plurality of known standard substances, a material of an object to be measured can be speculated even if a material of a standard sample is not necessarily the same as that of the object to be measured.

Figure 10:
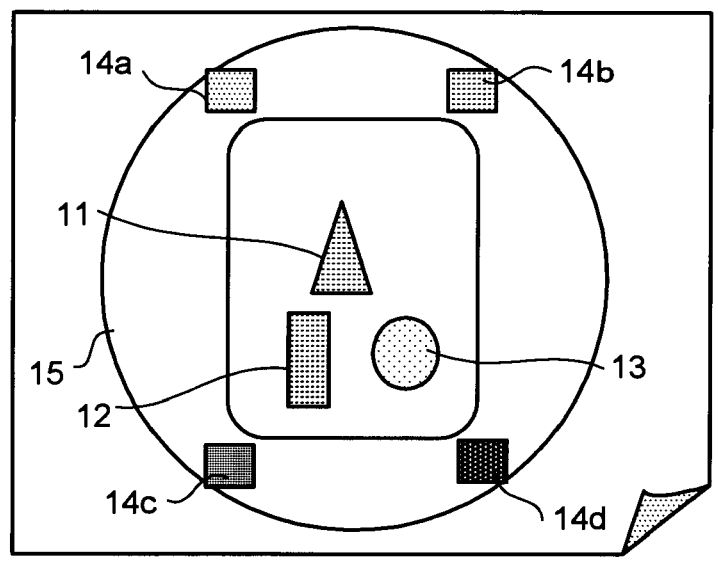
FIG. 10 is an explanatory diagram showing a disposition example of standard samples.

Next, a fifth embodiment will be described. In the present embodiment, the standard samples 14 in the first embodiment or the standard samples 18 in the second embodiment are disposed in four corners of a measurement area 15. In other words, when a sensor 4 is an area sensor, as shown in FIG. 10, usually a dead space necessarily occurs in somewhere in the measurement area 15, though depending on a shape of a sample 3. Thus, by disposing markers made of a material desired to be measured and in different thicknesses by several stages (for example, equal to or larger than three stages) as standard samples 14a to 14c in places (for example, in four corners or in four edges) giving only a small influence to an image within the measurement area 15 in advance, measurement can be performed without inserting standard samples every time.

Next, a sixth embodiment will be described. In the sixth embodiment, a line camera is used as the sensor 4 in the embodiment shown in FIG. 1 or FIG. 4. First, samples disposed as in FIG. 10 are scanned by the line camera to obtain an image, with energy of an x-ray being, for example, 150 keV. Subsequently, scanning is similarly performed with energy of the x-ray being 300 keV. Deviation of images by scanning can be corrected by the standard samples disposed in four corners. A line camera, unsimilarly to an area sensor, can obtain a large image by increasing a scanning length. According to the constitution as described above, identification of a material is possible regardless of a size of a sample.

INDUSTRIAL APPLICABILITY

A nondestructive identification method and a nondestructive identification device of the present invention can be used in a field of a radioactive waste processing in an atomic power plant, and so on. Therefore, the nondestructive identification method and the nondestructive identification device of the present invention have industrial applicability.

What is claimed is:

1. A nondestructive identification method configured to irradiate a radiation ray of an x-ray or a γ-ray from a radiation source to a sample, and to identify contents inside the sample from a transmission image of the radiation ray having transmitted the sample, the method comprising:
    obtaining a first transmission image by irradiating a radiation ray to the sample and one or more standard samples made of a known material, with energy of the radiation source being first energy;
    obtaining a second transmission image by irradiating the radiation ray to the sample and the one or more standard samples, with the energy of the radiation source being second energy different from the first energy;
    performing luminance adjustment on the second transmission image to make a luminance value of a part of the standard sample in the second transmission image be almost the same as a luminance value of a part of the standard sample in the first transmission image; and
    obtaining an image in which only a part of the same material as the standard sample is deleted, by taking a difference between the second transmission image on which the luminance adjustment is performed and the first transmission image.

2. The nondestructive identification method according to claim 1,
    wherein a plurality of materials are displayed by color, by using a sensor which is made of combination of a color-emitting scintillator and a color camera and which simultaneously photograph a plurality of images of different colors as a sensor to photograph the transmission image, and by performing luminance adjustment in order for deleting a different material for each component of the obtained plurality of transmission images.

3. The nondestructive identification method according to claim 1,
    wherein, whether an atomic number or a density of a major constitutional element is larger or smaller than that of a constitutional element of the standard sample is speculated depending on whether a luminance value of an unknown content part in the image in which only the part of the same material as that of the standard sample is deleted is a positive value or a negative value by taking a difference between the second transmission image to which the luminance adjustment has been done and the first transmission image.

4. A nondestructive identification method configured to irradiate a radiation ray of an x-ray or a γ-ray from a radiation source to a sample, and to identify contents inside the sample from a transmission image of the radiation ray having transmitted the sample, the method comprising:

by photographing a transmission image of a standard sample of known thickness and material and the sample while sequentially adding the standard samples with energy of the radiation source being first energy, and by photographing a transmission image of the standard sample and the sample while sequentially adding the standard samples with energy of the radiation source being second energy different from the first energy, obtaining a relation between the thickness of the standard sample in two types of energy and a luminance value of the transmitting radiation ray, and obtaining a function to make the luminance value obtained with the first energy in the transmission image of the standard sample be almost the same as the luminance value obtained with the second energy; and taking a ratio between an image made by applying the function to the entire transmission image obtained with the first energy and a transmission image obtained with the second energy, normalizing a luminance of a part of the standard sample to be a specific value.

5. The nondestructive identification method according to claim 4, wherein, whether an atomic number or a density of a major constitutional element is larger or smaller than that of a constitutional element of the standard sample is speculated depending on whether a luminance value of an unknown content in the image to which a computation processing to normalize a luminance value of the part of the standard sample to be 1 is performed is larger or smaller than 1.

6. A nondestructive identification method configured to irradiate a radiation ray of an x-ray or a γ-ray from a radiation source to a sample, and to identify contents inside the sample from a transmission image of the radiation ray having transmitted the sample, the method comprising:

by photographing a transmission image of a standard sample of known thickness and material and a sample while sequentially adding the standard samples, with energy of the radiation source being first energy, and by photographing a transmission image of the standard sample and the sample while sequentially adding the standard samples with energy of the radiation source being second energy different from the first energy, obtaining a relation between the thickness of the standard sample and a luminance value of the transmitting radiation ray in two types of energy; and comparing the relation of the luminance value for the thickness of the standard samples added before the sample and the relation between the thickness and the luminance value in only the standard sample, speculating a material and a thickness of the sample.

7. A nondestructive identification device, comprising:
one or more standard samples made of a known material;
a radiation source irradiating a radiation ray of an x-ray or a γ-ray to the standard sample and a sample, having a mechanism to change an energy of the radiation ray;
a sensor detecting the radiation ray having transmitted the standard sample and the sample;
a signal processing device converting a signal of the sensor into an image;
an image processing device which performs adjustment on an entire second image to make a luminance value of a part of the standard sample in the image obtained by the signal processing device or a relation between the luminance value and a thickness of the standard sample in a first image where the energy of the radiation source is first energy be the same as that in the second image where the energy of the radiation source is second energy different from the first energy, and which performs a computation processing to take a difference or a ratio between the adjusted second image and the first image; and a display device displaying an image on which the computation processing is performed by the image processing device.

8. The nondestructive identification device according to claim 7, wherein the sensor is constituted by combining a scintillator converting a radiation ray into a light, an amplification function converting the emitted light into an electric signal and electrically amplifying that electric signal, a color scintillator emitting lights of a plurality of colors in correspondence with an intensity of the electric signal, and a color camera; and wherein a plurality of materials is displayed by color by applying luminance adjustment to delete the different material for respective components of red, green, and blue of an obtained transmission image.

9. The nondestructive identification device according to claim 7, wherein the standard sample is made to be able to be photographed simultaneously with the sample by using an area camera as the sensor and by disposing the standard samples made of different materials or the standard samples having different thicknesses by three or more stages in four corners or four edges of a screen to be photographed, and a material inside the sample is identified by processing image data of a part of the standard sample in images photographed with the energy of the radiation ray being changed.

10. The nondestructive identification device according to claim 7, wherein the standard sample is made to be able to be photographed simultaneously with the sample by using a line camera as the sensor and by disposing the standard samples made of different materials or the standard samples having different thicknesses by three or more stages in both sides of or above and below the sensor to photograph, and a material inside the sample is identified by processing image data of a part of the standard sample in an image photographed with the energy of the radiation ray being changed.

11. A nondestructive identification device, comprising:
a standard sample a known material and thickness;
a radiation source irradiating a radiation ray of an x-ray or a γ-ray to the standard sample and a sample, having a mechanism to change an energy of the radiation ray;
a sensor detecting the radiation ray having transmitted the standard sample and the sample; and
a signal processing device converting a signal of the sensor into an image,
wherein the thickness of the standard sample and the energy of the radiation source are changed and a transmission image is measured each time, and a material and a thickness of the sample is derived from change of a luminance of the image by the thickness of the standard sample and the energy of the radiation source.

* * * * *